United States Patent [19]

Lind

[11] Patent Number: 5,067,489
[45] Date of Patent: Nov. 26, 1991

[54] FLEXIBLE GUIDE WITH SAFETY TIP

[75] Inventor: Stuart J. Lind, Minneapolis, Minn.

[73] Assignee: Flexmedics Corporation, Minneapolis, Minn.

[21] Appl. No.: 604,360

[22] Filed: Oct. 26, 1990

Related U.S. Application Data

[63] Continuation of Ser. No. 232,721, Aug. 16, 1988, abandoned.

[51] Int. Cl.$^5$ .............................................. A61B 5/00
[52] U.S. Cl. ...................................... 128/772; 604/164
[58] Field of Search ................. 128/657, 772; 604/95, 604/164, 170, 280, 282

[56] References Cited

U.S. PATENT DOCUMENTS

| | | | |
|---|---|---|---|
| 3,452,742 | 7/1969 | Muller | 128/657 |
| 3,521,620 | 7/1970 | Cook | 128/772 |
| 3,612,058 | 10/1971 | Ackerman | 128/772 |
| 3,625,200 | 12/1971 | Muller | 128/772 |
| 3,749,086 | 7/1973 | Kline et al. | 128/772 |
| 3,789,841 | 2/1974 | Antoshkiw | 128/772 |
| 3,841,308 | 10/1974 | Tate | 128/772 |
| 3,906,938 | 9/1975 | Fleischhacker | 604/170 |
| 4,003,369 | 1/1977 | Heilman et al. | 128/772 |
| 4,020,829 | 5/1977 | Willson et al. | 128/657 |
| 4,080,706 | 3/1978 | Heilman et al. | 128/772 |
| 4,456,017 | 1/1984 | Miles | 128/772 |
| 4,534,363 | 8/1985 | Gold | 128/772 |
| 4,545,390 | 10/1985 | Leary | 128/772 |
| 4,554,929 | 11/1985 | Samson et al. | 128/772 |
| 4,579,127 | 4/1986 | Haacke | 128/772 |
| 4,619,274 | 10/1986 | Morrison | 128/657 |
| 4,724,846 | 2/1988 | Evans, III | 128/657 |
| 4,776,844 | 10/1988 | Ueda | 604/95 |
| 4,811,743 | 3/1989 | Stevens | 128/657 |
| 4,854,330 | 8/1989 | Evans, III et al. | 128/772 |
| 4,925,445 | 5/1990 | Sakamoto et al. | 604/95 |

FOREIGN PATENT DOCUMENTS 1232814  2/1988  Canada ............................... 128/657

Primary Examiner—Randy Citrin Shay
Attorney, Agent, or Firm—James R. Haller; Gregory P. Kaihoi; Edward S. Hotchkiss

[57] ABSTRACT

An elongated guide for use in medical procedures is provided, the guide having a flexible metal core and a forward portion comprising an elongated, helically wound wire coil providing a flexible tip. A flexible safety wire extends forwardly within the coil and terminates forwardly in an integral, enlarged diameter portion defining a plug carried adjacent the forward end of the coil, the plug having a diameter at least approximately equal to the inner diameter of the coil at its forward end and substantially filling the lumen of the coil. A bonding agent such as a polymeric resin, solder or the like is employed to adhere the plug to the coil.

7 Claims, 1 Drawing Sheet

FLEXIBLE GUIDE WITH SAFETY TIP

This application is a continuation of application Ser. No. 232,721, filed Aug. 16, 1988, now abandoned.

BACKGROUND OF THE INVENTION

Elongated, flexible guide units are often used in medical procedures to gain access to specific inner areas of the body without major surgery. Guide units may be passed into the body via peripheral blood vessels, the gastrointestinal tract, or the urinary tract. Guide units, often referred to as guide wires, are commercially available and are currently used in cardiology, gastroenterology, urology, and radiology. Once in place, guide wires serve as guides for the safe introduction of additional medical instruments such as catheters.

To facilitate threading a guide through a predetermined body channel such as an artery, the guide may include a generally flexible body portion which is resistant to kinking and a forward end portion of increased flexibility, the end portion terminating in a smoothly rounded tip. The body portion may include a core of stainless steel or other metal, the core being appropriately dimensioned in cross section to provide the desired degree of flexibility to the guide wire. A coating of plastic or the like may be applied over the surface of the core, if desired. To provide greater flexibility to the guide at its forward end, the forward end of the core may include a section of lesser diameter and hence of greater flexibility. Optionally, the core may terminate at a position spaced from the guide end, thus providing the guide end with increased flexibility. A flexible length of helically wound wire forming an elongated coil ma be employed at the forward end of the guide wire and may extend throughout the length of the guide unit. A small button or plug commonly is employed at the forward end of the coil to provide the guide with a smoothly rounded tip.

When a guide is to be removed from a body channel such as an artery, the forward, end of the guide can unintentionally become detached from the body of the guide wire and hence may remain behind in the artery when the guide wire is withdrawn. In an attempt to prevent this from occurring, researchers have employed safety wires which may extend substantially throughout the length of a catheter and which are soldered or otherwise adhered to the forward button so that the button and coil can be retrieved together with the remainder of the guide wire when the latter is withdrawn from an artery. The safety wire may be of a flattened wire and may lie along side the core Alternatively, the metal core may have a tapered, forward end portion that functions as a safety wire and that is attached to the forward button. Reference is made particularly to U.S. Pat. No. 4,003,369 and 3,612,058 as showing guide wire embodiments of the type described.

Unfortunately, the attachment via solder or other adhesive of safety wires to the forward buttons in guide wires of the type described generally is not particularly strong. It appears that failure occurs generally in the soldered or other adhesive bond between the forward end of the safety wire an the metal button at the forward end of the guide wire. It would be desirable to provide a flexible guide having a forward tip which is far more securely fastened to the body of the guide.

SUMMARY OF THE INVENTION

The present invention provides an elongated flexible guide having a flexible metal core and a forward portion that comprises an elongated, helically wound wire coil providing a flexible tip. The guide includes a flexible safety wire extending forwardly within the coil and terminating forwardly in an integral enlarged diameter portion defining a plug carried adjacent the forward end of the coil and having a diameter at least approximately equal to the inner diameter of the coil at its forward end, the plug substantially filling the lumen of the coil. The plug, of generally circular cross section, is coaxial and is radially symmetrical with respect to the interior of the coil. A bonding agent such as solder, a polymer, a cement or other adhesive is employed to adhere the plug to the coil.

In a preferred embodiment, the flexible metal core has a forward end portion of reduced diameter to provide greater flexibility, the reduced diameter portion of the core extending within the coil and terminating forwardly in an integral enlarged diameter portion defining the plug. In this embodiment, the core of the guide wire itself functions as the safety wire to prevent loss of the forward end elements of the guide when it is withdrawn from a body channel. The core preferably is formed of a shape memory alloy such as nitinol.

DETAILED DESCRIPTION OF THE PREFERRED EMBODIMENTS

Figure 1:
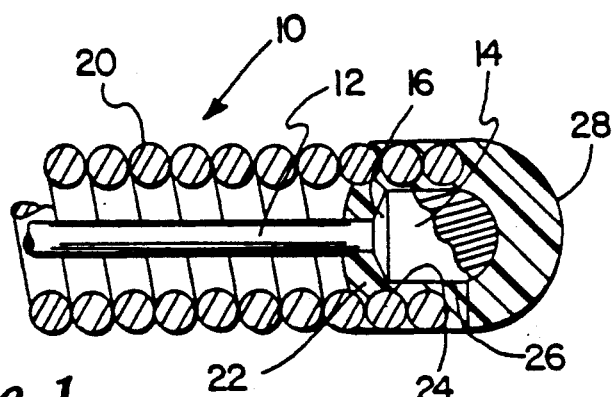
FIG. 1 is a broken-away cross sectional view of an end portion of a guide of the invention.
Figure 2:
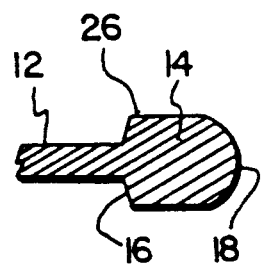
FIG. 2 is a broken-away cross sectional view of the forward end of a safety wire shown also in FIG. 1.

The guide wire 10 shown in FIG. 1 includes a core wire having a forward end 12 of reduced diameter and which terminates forwardly in a cylindrically shaped plug 14. The plug is generally circular in cross section, as desirably is the reduced diameter forward portion 12 of the core. As shown in FIG. 2, the core and the plug are integrally formed, the plug representing an enlarged diameter portion of the core and the change in diameters providing the plug 14 with a generally rearwardly facing annular shoulder 16. The shoulder 16 may be in a plane generally perpendicular to the axis of the plug 14, or may be tapered as shown in FIGS. 1 and 2. The forward end 18 of the plug may be generally rounded as shown in the drawing.

The flexible forward portion of the guide shown in FIG. 1 includes an elongated, helically wound wire coil 20, the helically wound wire being of circular cross section as shown in the drawing or of any other convenient cross section such as the flattened cross sections appearing in U.S. Pat. Nos. 4,003,369 and 4,080,706, the teachings of which are incorporated herein by reference. The elongated, helically wound coil may extend only through the flexible tip portion of the guide or may extend the entire length of the guide. The elongated, helical coil of a metallic wire such as stainless steel is provided not only to lend flexibility to the forward tip of the guide but also to provide a radio opaque guide tip which can be readily viewed by means of x-rays. The helical coil has an inner diameter at its forward (right-hand) end that is substantially equal to the outer diameter of the plug 14 such that the plug can be snugly received within the forward end of the coil to occupy the entire lumen of the coil. A bonding agent 22, such as an epoxy resin, is employed to bond the plug to the coil. As shown in FIG. 1, the bonding agent 22 extends between and bonds together confronting surfaces 24, 26 of the core and plug, respectively. The bonding agent desirably extends within the coil rearwardly of the plug a shown in FIG. 1 and contacts the rearwardly facing annular shoulder 16 of the plug such that when the core is pulled to the left in FIG. 1 (as when the guide is to be removed from a patient), the bonding agent that extends rearwardly of the plug is placed under compressive stress. It will be understood that the plug and the forward portion of the elongated, helical coil are radially symmetrical and, accordingly, compression, tensile and shear forces placed upon the bonding agent 22 are circumferentially fairly evenly distributed, the bonding agent thus providing a strong bond between the coil and plug. Also, since the forward end 12 of the core and the plug are integrally formed as shown in FIG. 2 and hence are free of solder joints or the like, the possibility of the plug separating from the forward end of the core is substantially reduced in comparison to guide wires in which the forward end of the core or other safety wire is soldered or brazed to a forward button.

In the embodiment of FIG. 1, the bonding agent 22 extends forwardly of the plug 14 and provides the guide wire 10 with a gently rounded forward tip 28. The bonding agent may be a solder which is used to solder or braze the plug to the coil end, the solder serving to strongly adhere the confronting surfaces of the plug and normally forming a generally spherical forward end 28. The bonding agent preferably is polymeric, however, and may be a hardenable resin such as an epoxy resin. The solder or resin or other bonding material desirably extends rearwardly for only a few turns of the coil, as shown. The forward or tip end 28 of the guide shown in FIG. 1 may be formed of a metallic material, or may be of a polymeric resin such as an epoxy resin. Thus, the tip portion 28 and the rearward portion 22 of the bonding agent may be of the same material or of different material, the harder, solder like material being employed for the tip 28 forwardly of the forwardmost turn of the helical coil and the remainder of the bonding material being formed of a polymeric binder such as an epoxy resin. Desirably, the tip 28 and the remainder of the bonding material are identical. Epoxy resins, commercially available, which harden upon cure, are preferred bonding agents.

The core wire employed in guides of the invention desirably is made of a shape memory alloy which exhibits superelastic/pseudoelastic shape recovery characteristics. Such alloys are known in the field and are characterized by their ability, at a desired temperature, to be deformed from an austenitic crystal structure to a stress-induced martensitic structure, returning to the austenitic state when the stress is removed. The alternate crystal structures provide the alloy with superelastic or pseudoelastic properties. Alternatively, a cold-worked martensitic microstructure can be used to provide enhanced shape recovery and a lower stiffness, than, for example, stainless steel. Nitinol, an alloy of nickel and titanium, is particularly preferred in that it is commercially available and has been studied somewhat more than other shape memory alloys. If desired, however, the core can be made out of other springy metal material such as stainless steel and the like. Shape memory alloys are preferred because of their capacity to elastically recover almost completely an initial configuration. That is, shape memory alloys have the capacity to avoid taking a "set" when deformed; in this manner, a guide wire of the invention having a core of shape memory alloy may be substantially straight when unstressed, may elastically deform as it passes through curved body channels, and yet will recover its straight configuration when stress is removed. Shape memory alloys in general, and nitinol in particular, can be soldered or brazed only with some difficulty and the solder joint that results is not of great strength. Hence, the formation of an integral plug at the end of a safety wire as is used in the instant invention avoids the necessity of soldering or otherwise attaching the end of the safety wire to a plug or button, and the plug hence is far more resistant to being pulled from the end of the safety wire. In a test of various guide wires in which safety wires were led forwardly through a flexible helical coil tip and were then inserted into small recesses formed in the rearward side of the button and soldered or brazed in place (the buttons being of a diameter approximately equal to the outer diameter of the coil), tensile break strengths (holding the coil stationary and pulling rearwardly upon the core wire or safety wire) on the order of 2.0-3.5 pounds were measured. A device similar to that shown in U.S. Pat. No. 3,612,058, employing a central core wire extending forward within a helical coil, the core wire having a bend in its forward end and being there adhered to the coil, exhibited a tensile strength on the order of 1.5 pounds. A guide of the invention made in accordance with FIG. 1, however, having a plug 14 substantially filling the lumen of the coil and being adhered to the coil, exhibited a tensile strength of about 7 pounds.

Figure 3:
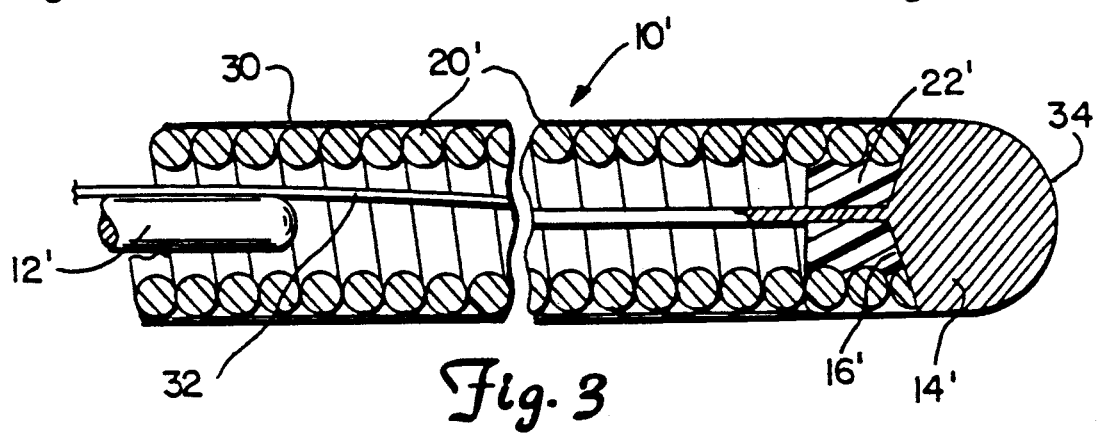
FIG. 3 is a broken-away cross sectional view of an end portion of another embodiment of the invention.

FIG. 3 illustrates the forward end portion of another guide of the invention, and similar but primed (') numbers are used to designate elements that are similar to those shown in FIGS. 1 and 2. The guide of FIG. 3 includes an elongated helical coil 20', and may optionally include an outer polymeric coating 30 of polytetrafluoroethylene or other polymeric material. The helical coil 20 may extend only through the end length of the guide or may extend the entire length of the guide, as desired. The guide includes a central core having a forward end 12' which terminates forwardly at a position spaced from the forward end of the helical coil. The forward end portion 12' of the core is illustrated as being rounded, but it will be understood that the core can be shaped so as to taper forwardly as well. Shown at 32 in FIG. 3 is a safety wire which may extend the entire length of the guide. The safety wire preferably is a flattened wire which lays snugly against the core 12', the safety wire extending forwardly through the forward end 20 of the helical coil. Near its forward end, the safety wire 32 undergoes an abrupt increase in diameter to form a plug 14', the plug having a generally cylindrical configuration. The rapid increase in diameter of the plug provides it with a generally rearwardly facing shoulder 16', and the outer diameter of the plug 14 is substantially equal to the outer diameter of the coil at its forward end so that the shoulder 16 of the plug bears rearwardly against the forward end of the coil. A bonding agent 22', preferably a polymer such as an epoxy resin, is provided between the forward end of the coil and the shoulder 16 to bond the plug to the forward end of the coil. The plug 14 itself has a gently rounded, preferably spherical forward surface 34. The embodiment of FIG. 3 provides a mechanical linkage between the plug and the coil 20', the rearwardly facing shoulder 16' of the plug bearing mechanically rearwardly against the coil. Again, the safety wire 32 is formed integrally with the plug 14', and weaknesses associated with brazing or soldering of the safety wire to a leading button is hence avoided. Also, the core 12 of the embodiment of FIG. 3 is preferably of a shape memory alloy such as nitinol.

Figure 4:
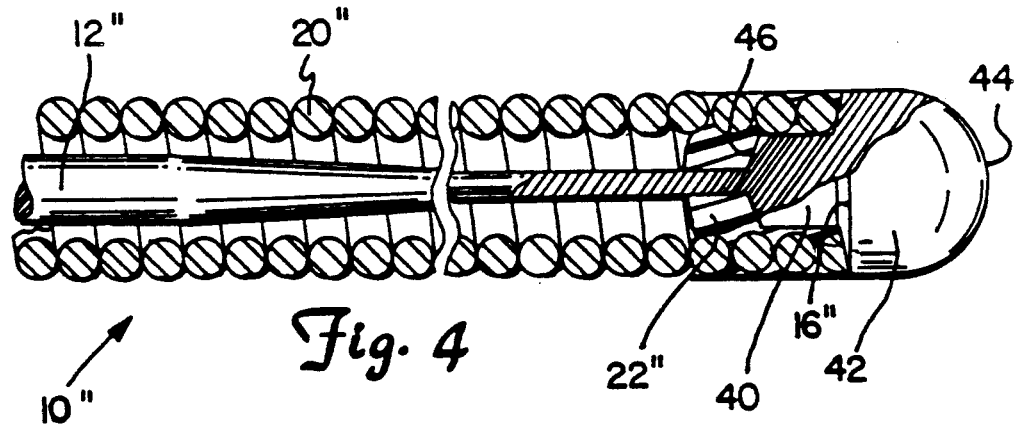
FIG. 4 is a broken-away view of a end portion of yet another embodiment of the invention.

Another embodiment of a guide of the invention is illustrated in FIG. 4. Similar numbers (bearing double primes (")) are employed to designate elements that are similar to those shown in FIGS. 1 and 3. In the embodiment of FIG. 4, a core 12" extends forwardly through the interior of an elongated helical coil 20", the core having a generally circular cross section and the diameter of the coil decreasing forwardly as depicted, the forward end of the core serving as a safety wire as will now be described. Near its forward end, the diameter of the core increases abruptly to form a cylindrical plug portion 40 having a rearwardly facing annular shoulder 46, the plug portion 40 having a diameter approximately equal to the inner diameter of the coil 20" at its forward end and being receivable snugly within the forward end of the coil to occupy substantially the entire lumen of the coil. The core, proceeding forwardly, undergoes another abrupt change in diameter to form a forward plug portion 42 having a rearwardly facing annular shoulder 16" and a smoothly rounded forward end 44 similar to that shown at 34 in FIG. 3. The diameter of the forward plug portion 42 is substantially the same as the outer diameter of the coil 20" at its forward end, and the annular shoulder 16" bears rearwardly against the forward end of the coil 20". The rearward plug portion 40 serves to center the plug as a whole with respect to the end of the core, and a bonding agent 22" such as an epoxy resin is provided between confronting surfaces of the rearward plug portion 40 and the coil and also rearwardly of the annular shoulder 46, in a manner similar to that shown in the embodiment of FIG. 1. As with the embodiments of FIGS. 1 and 3, the plug of the embodiment of FIG. 4 is formed integrally with the safety wire (shown as the forward end of the core). Thus, the embodiment of FIG. 4 incorporates the self-centering and strong bond characteristics of the embodiment of FIG. 1 and the mechanical linkage of FIG. 3. Again, the plug utilized in the embodiment of FIG. 4 is formed integrally with the safety wire formed as the forward end of the core 12", the latter desirably being formed of a shape memory alloy.

It will be understood that the embodiments of FIGS. 1-4 are illustrative only. The rearwardly facing annular shoulders 16 (FIG. 1), 16' (FIG. 3) and 16' and 46 (FIG. 4) may be formed approximately as shown in the drawing, may extend in planes generally normal to the axes of the plugs, or may taper rearwardly more gently to merge into the forward ends of the safety wires. The present invention, by virtue of utilizing an integrally formed safety wire and plug, the latter substantially filling the lumen of an elongated, forwardly extending helical coil, provides a strong connection between the safety wire and the forward end of the guide so as to more fully prevent loss of the forward end of the guide within a vein or other body channel when the guide is drawn from the vein.

While a preferred embodiment of the present invention has been described, it should be understood that various changes, adaptations and modifications may be made therein without departing from the spirit of the invention and the scope of the appended claims.

What is claimed is:

1. A guide wire comprising an elongated flexible metal core, an elongated, helically wound wire coil having a forward end and providing the guide wire with a flexible tip, the core having a forward portion of reduced diameter extending forwardly within the tip and terminating forwardly in an enlarged diameter portion integrally formed with the core and defining a plug carried adjacent the forward end of the coil, the plug having a diameter approximately equal to the inner diameter of the coil at its forward end and substantially filling the inner lumen of the coil adjacent its forward end, and a bonding agent bonding the plug to the coil.

2. The guide wire of claim 1 wherein the core is of shape memory alloy.

3. The guide wire of claim 1 further comprising an exposed, gently rounded tip portion carried forwardly of the plug and adapted to contact tissue during use of the guide wire.

4. The guide wire of claim 1 wherein the bonding agent extends between the annular shoulder and the coil so as to be placed in compression when the core is pulled rearwardly with respect to the coil.

5. A guide wire comprising an elongated flexible metal core, an elongated, helically wound wire coil having a forward end providing a flexible tip, the flexible metal core having a forward portion of reduced diameter extending forwardly within the tip and terminating forwardly in an enlarged diameter portion integrally formed with the core and defining a plug carried adjacent the forward end of the coil and having a diameter approximately equal to the inner diameter of the coil and substantially filling the inner lumen of the coil adjacent its forward end, the plug having a rearwardly facing annular shoulder, and a bonding agent bonding the plug to the coil, the bonding agent extending between said annular shoulder and the coil so as to be placed in compression when the safety wire is pulled rearwardly with respect to the coil.

6. The guide wire of claim 5 wherein the core is of shape memory alloy.

7. The guide wire of claim 5 further comprising an exposed, gently rounded tip portion carried forwardly of the plug and adapted to contact tissue during use of the guide wire.

* * * * *